United States Patent [19]

Flesher

[11] Patent Number: 5,149,418
[45] Date of Patent: Sep. 22, 1992

[54] VERTICAL GEL ELECTROPHORESIS APPARATUS HAVING UNIVERSAL GEL ASSEMBLY SUPPORT STRUCTURE

[75] Inventor: Robert W. Flesher, Baltimore, Md.

[73] Assignee: Apogee Designs, Ltd., Baltimore, Md.

[21] Appl. No.: 754,530

[22] Filed: Sep. 4, 1991

[51] Int. Cl.⁵ .................... B01D 61/42; C25D 13/00
[52] U.S. Cl. .................... 204/299 R; 204/182.8
[58] Field of Search .................... 204/182.8, 299 R

[56] References Cited

U.S. PATENT DOCUMENTS

| | | | |
|---|---|---|---|
| 3,980,540 | 9/1976 | Hoefer | 204/180 G |
| 4,337,131 | 6/1982 | Vesterberg | 204/180 G |
| 4,772,373 | 9/1988 | Ebata et al. | 204/299 R |
| 4,773,984 | 9/1988 | Flesher et al. | 204/299 R |
| 4,874,490 | 10/1989 | Hochstrasser | 204/182.1 |
| 4,929,329 | 5/1990 | Danby et al. | 204/299 R |
| 4,957,613 | 9/1990 | Schuette | 204/299 R |
| 4,975,174 | 12/1990 | Bambeck et al. | 204/299 R |
| 4,994,166 | 2/1991 | Fernwood et al. | 204/299 R |
| 5,013,420 | 5/1991 | Schuette | 204/299 R |

OTHER PUBLICATIONS

Mini Protein Systems Advertisement.
Mini-V 8-10 Vertical Gel Electrophoresis System, Life Technologies, Inc.
Mini Vertical Slab Gel Electrophoresis Unit, Buchler Instruments.

*Primary Examiner*—John Niebling
*Assistant Examiner*—Caroline Koestner
*Attorney, Agent, or Firm*—Fleit, Jacobson, Cohn, Price, Holman & Stern

[57] ABSTRACT

A vertical gel electrophoresis apparatus featuring a support plate mounted in a buffer solution container, the support plate securing a gel assembly in position and dividing the container into two laterally juxtaposed isolated chambers. The support plate includes two vertical support members which are mounted along opposite vertical sides of the container, and an integral support member mounted along the bottom of the container. A face is cut in each vertical support member to receive opposite vertical edges of a gel assembly. The integral bottom support member includes a face terminating at flanges proximate the vertical support members. The bottom edge of the gel assembly rests on the flanges over the face of the integral bottom support member. The gel assembly is sealed against the integral bottom support member isolating the top opening of the gel assembly from the bottom opening and the gel assembly effectively separates the container into two chambers with the bottom opening being exposed in one electrically charged chamber and the top opening being exposed in the other electrically charged chamber of the opposite polarity.

8 Claims, 3 Drawing Sheets

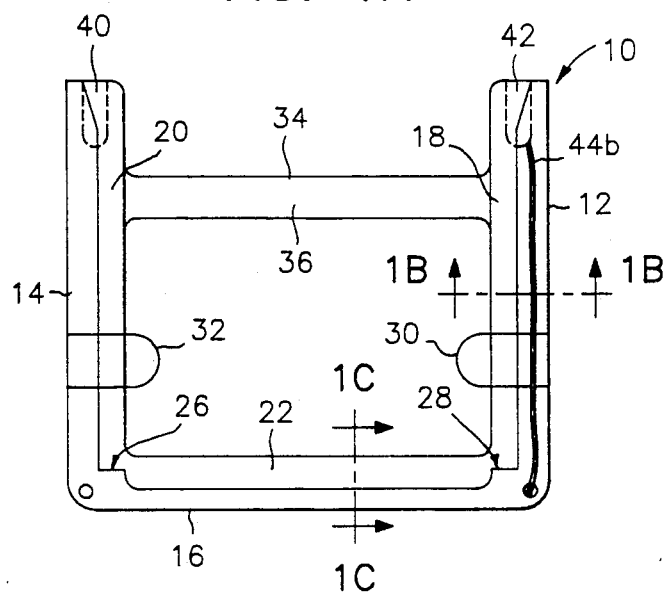
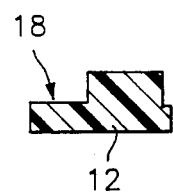
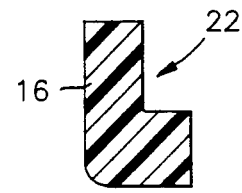
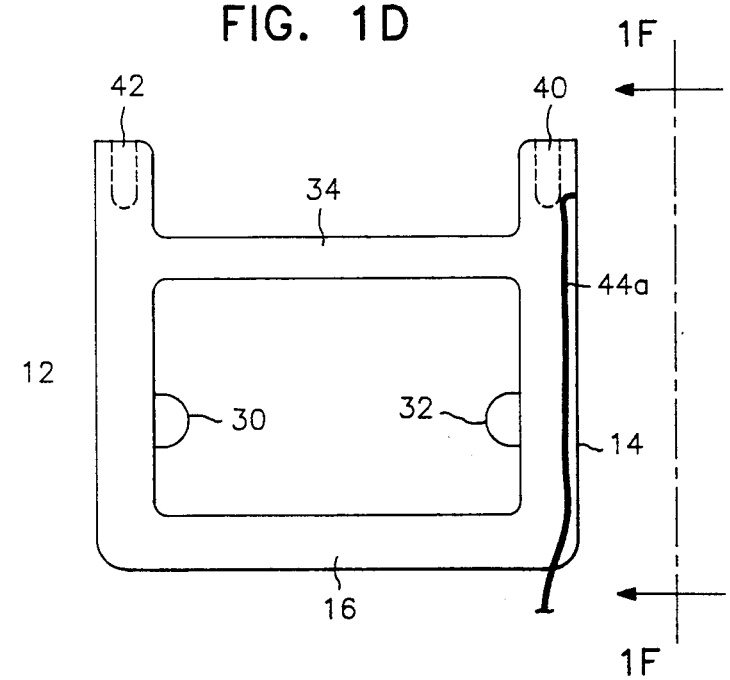
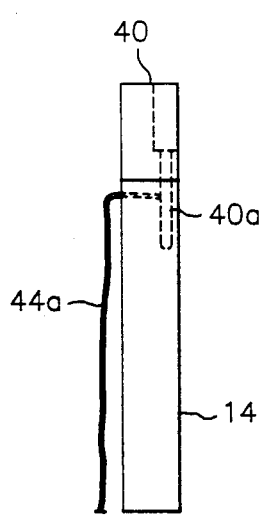
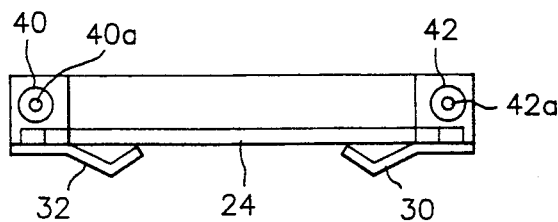

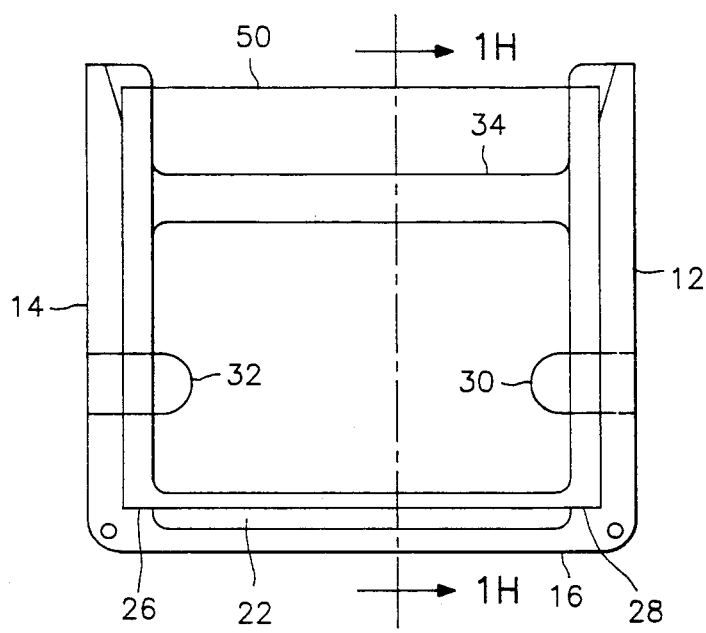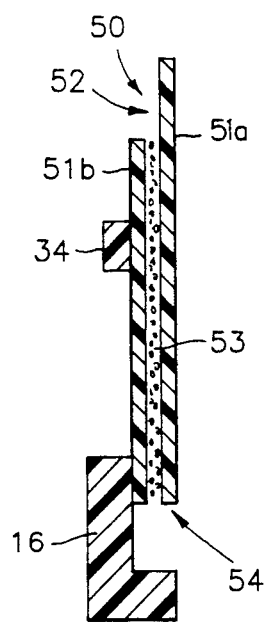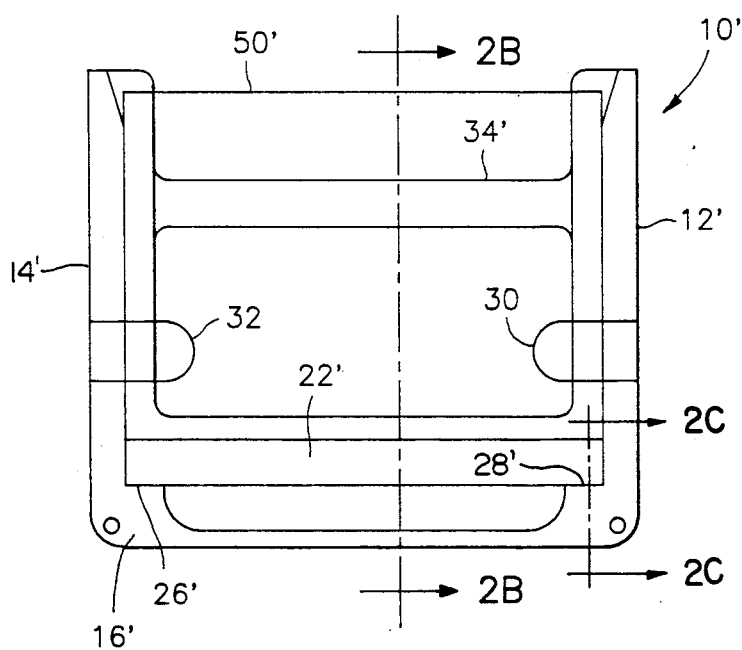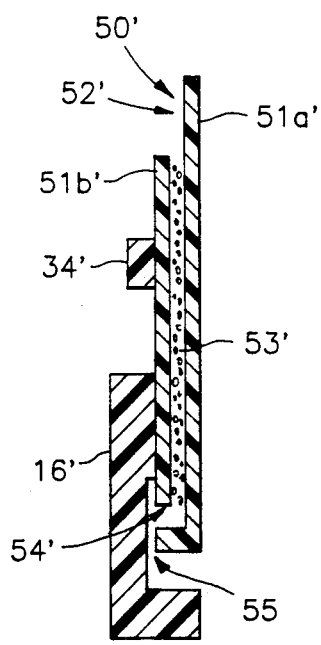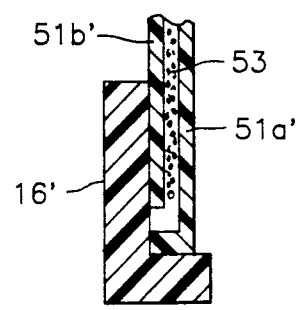

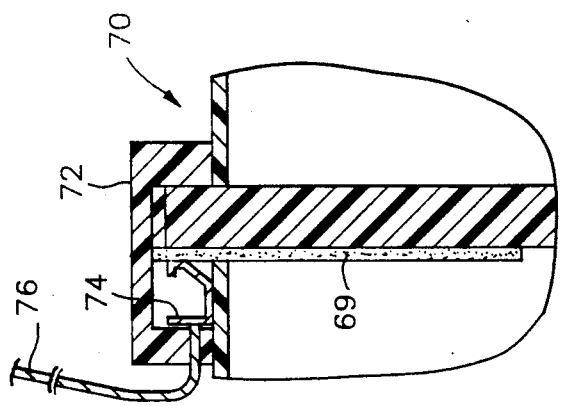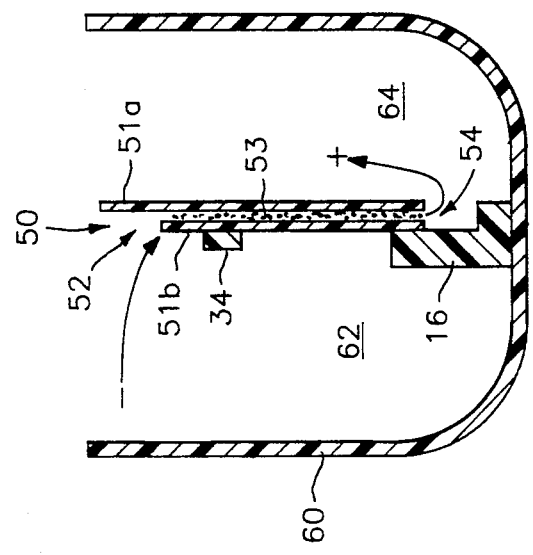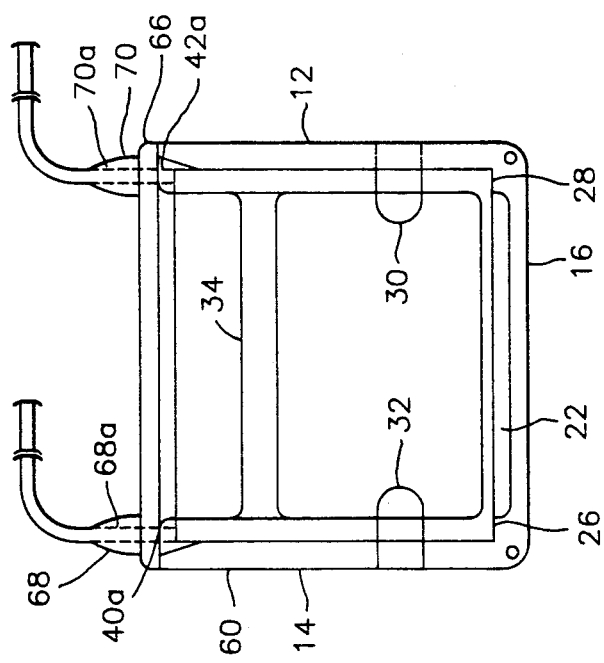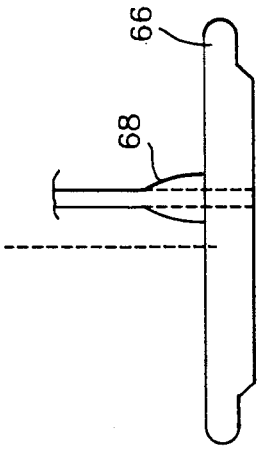

VERTICAL GEL ELECTROPHORESIS APPARATUS HAVING UNIVERSAL GEL ASSEMBLY SUPPORT STRUCTURE

BACKGROUND OF THE INVENTION

The present invention relates to a vertical gel electrophoresis apparatus, and more particularly, to an electrophoresis apparatus having structure capable of receiving pre-cast gel assemblies of multiple types.

In an electrophoresis apparatus, a gel assembly is secured between two bodies of buffer solution. Samples are inserted in wells formed within the gel. An electric field is applied between opposite ends of the gel assembly via the buffer solution causing the sample to migrate from the negative end of the gel to the positive end. A critical feature of an electrophoresis apparatus is the manner in which the gel assembly is supported.

Currently, there are electrophoresis devices known which provide rather elaborate clamping mechanisms for securing the gel assembly in place between two chambers of buffer solution. See, for example, U.S. Pat. Nos. 4,773,984 to Flesher et al., 4,975,174 to Banbeck et al., 4,929,329 to Danby et al., and 4,957,613 to Schuette. While such clamping mechanisms serve their purpose for specific gel assemblies, the need arises to use pre cast gel assemblies from many manufacturers in a single electrophoresis device. It is desirable that the device be designed to receive assemblies of different thicknesses and designs. It has been found that specialized clamping mechanisms hamper the ability to adapt to a variety of gel assemblies and add unnecessary complexity to the apparatus.

SUMMARY OF THE INVENTION

It is, therefore, a primary object of the present invention to provide an electrophoresis apparatus which is capable of receiving a variety of gel assemblies of differing thickness.

It is another object of the present invention to provide an electrophoresis apparatus which is designed to fit a variety of gel assemblies without complex clamping mechanisms.

Briefly, the present invention is directed to a vertical gel electrophoresis apparatus featuring a support plate mounted in a buffer solution container, the support plate securing a gel assembly in position and dividing the container into two isolated chambers. The support plate includes two vertical support members which are mounted along opposite vertical walls of the container, and an integral bottom support member mounted along the bottom wall of the container. A groove is cut in each vertical support member to receive opposite vertical edges of a gel assembly. The integral bottom support member includes a groove terminating at flanges proximate the vertical support members. The bottom edge of the gel assembly rests on the flanges over the groove of the integral bottom support member.

The gel assembly is sealed against the integral bottom support member isolating the top opening of the gel assembly from the bottom opening and the gel assembly effectively separates the container into two chambers with the bottom opening being exposed in one chamber and the top opening being exposed in the other chamber. Thus, current flow through the gel assembly can be provided via the buffer solution in each chamber.

In the first embodiment, the support plate is designed to receive a gel assembly having a top opening facing to one side and a bottom opening facing the opposite side. In the second embodiment, the support plate is designed to receive a gel assembly having a top opening and a bottom opening, both on the same side of the assembly.

Resilient clip members are mounted on the vertical support members to hold the gel assembly firmly against the integral bottom and side support members. The clip members flex to accommodate gel assemblies of various thicknesses, but require no adjustment.

In accordance with a third embodiment, a structural arrangement is disclosed which eliminates the need of plug assemblies.

The above and other objects and advantages will become more readily apparent when reference is made to the following description taken in conjunction with the accompanying drawings.

BRIEF DESCRIPTION OF THE DRAWINGS

FIG. 1A is a front view of a gel assembly support plate forming part of the electrophoresis apparatus according to a first embodiment of the present invention.

FIG. 1B is a cross-sectional view taken through line 1B—1B of FIG. 1A.

FIG. 1C is a cross-sectional view taken through line 1C—1C of FIG. 1A.

FIG. 1D is a rear view of the gel assembly support plate shown in FIG. 1A.

FIG. 1E is a top view of the support plate shown in FIG. 1A.

FIG. 1F is a side view as seen from line 1F—1F of FIG. 1D.

FIG. 1G is a front view of the support plate shown in FIG. 1A with a gel assembly inserted therein.

FIG. 1H is a cross-sectional view taken through line 1H—1H of FIG. 1G.

FIG. 2A is a front view of a support plate in accordance with a second embodiment of the present invention, with a gel assembly inserted therein.

FIG. 2B is a cross-sectional view taken through line 2B—2B of FIG. 2A.

FIG. 2C is a cross-sectional view taken through line 2C—2C of FIG. 2A.

FIG. 3 is a front view of the electrophoresis apparatus including a support plate structure according to the present invention.

FIG. 4 is a cross-sectional view of the electrophoresis apparatus of shown in FIG. 3 and illustrating the flow of current through the gel assembly.

FIG. 5 is a side view of a modified lid of an electrophoresis apparatus according to the present invention.

FIG. 6 is a cross-sectional view of an electrophoresis apparatus including a modified support plate structure and cover in accordance with a third embodiment of the present invention.

DETAILED DESCRIPTION OF THE DRAWINGS

Referring first to FIGS. 1A-1H, the support plate of the vertical gel electrophoresis apparatus according to the present invention is generally shown at 10. As is well known in the art, an electrophoresis apparatus comprises a buffer container for supplying current through the gel assembly. The support plate 10 supports a gel assembly to be tested.

Accordingly, the support plate 10 of the electrophoresis apparatus of the present invention is designed to mate with several types of gel assemblies and to seal the gel assembly to the support plate preventing current migration from side-to-side, allowing for maximum efficiency. The support plate 10 comprises two vertical support members 12 and 14 and an integral bottom support member 16, formed integrally from well known plastic material. Vertical faces 18 and 20 for receiving vertical edges of a gel assembly are machined in the front side of the vertical support members 12 and 14, respectively. The surfaces of these faces form a sealing surface for the gel assembly, which sealing surface will be described in more detail hereinafter. Likewise, a horizontal face 22 is machined in the integral bottom support member 16, which also serves as a sealing surface.

The vertical faces 18 and 20 meet with the horizontal face 22 and form a slot 24 (FIG 1E) for receiving a gel assembly from the top of the support plate 10. Flanges 26 and 28 terminate the face 22 at the vertical support members 14 and 12, respectively. These flanges serve to support the bottom of the vertical edges of a gel assembly, but still allow electrical current access to a bottom opening of the gel assembly.

Two resilient clips 30 and 32 are attached to the vertical support members 12 and 14 and extend inwardly over the slot 24 for clamping a gel assembly into the support member 10. Furthermore, a horizontal support bar 34 is provided which is integrally formed with the vertical support members 12 and 14 and is labelled on the front surface 36 thereof to indicate the orientation for inserting the gel assembly into the support plate 18. The support bar 34 may also be colored on surface 36 to provide a background against which the samples to be loaded into the gel can be viewed. The support bar 34 is an optional structural feature.

Formed in each vertical support member is a plug assembly 40, 42 as shown in FIGS. 1E and 1F. Such plug assemblies are well known in the art, and comprises conductor pins 40a, 42a which extend downward into the support member. Electrical conductors 44a, 44b (FIGS. 1A, 1D and 1F) are connected to the conductor pin of each plug assembly and extend down opposite sides of the support plate 10, where a respective body of buffer solution is to be provided. The top of each conductor pin serves as a male plug member to connect with a female plug member, to be described hereinafter.

Turning now to FIGS. 1G and 1H, the manner in which a gel assembly is inserted and sealed into the support plate 10, will be described. The gel assembly, shown at 50, is comprised of two plates 51a and 51b, one of which is longer than the other to provide a top opening 52 on one side of the assembly and a bottom opening 54. The gel 53 is supported between the plates 51a and 51b. The gel assembly is inserted into the slot 24 and rests on the flanges 26 and 28. The plate 51b of the gel assembly seals against the surfaces of the vertical faces 18 and 20 and the horizontal face 22. As a result, the top opening 52 of the gel assembly 50 is exposed only on the left side of the support plate 10 (as shown in FIG. 1H), while the bottom opening 54 is exposed only on the right side of the support plate 10. Each side of the gel assembly is filled with a conductive buffer solution once the assembly is secured in position.

FIGS. 2A–2C illustrate a support plate structure in accordance with a second embodiment of the invention. In particular, support plate 10' is similar to support plate 10, but is designed to secure a slightly different type of gel assembly. Gel assembly 50' comprises two plates 51a' and 51b' in which the top opening 52' and the bottom opening 54' are on the same side of the gel assembly. To isolate the two openings for access by a respective body of buffer solution, a modification is made to the support plate 10.

Specifically, the face 22' in the integral bottom support member 16' is cut deeper and into the thickness of the support member 16' creating a gap 55 so that the plate 51b' seals against the support member 16' above the bottom opening 54', as shown in FIG. 2B. However, flanges 26' and 28' support the assembly at the vertical edges thereof, as shown in FIG. 2C. The support plate 10' thereby isolates the top opening 52' from the bottom opening 54', to allow access to the respective bodies of buffer solution.

FIGS. 3 and 4 illustrate an electrophoresis apparatus including the support plate structure of the first or second embodiments according to the present invention. The support plate (10 or 10') is sealed into or otherwise formed as part of a container 60 and with a gel assembly 50 or 50' inserted therein. Specifically, the vertical support members 12 and 14 are mounted across opposite vertical walls of a container 60 and the integral bottom support member is mounted on the bottom wall of the container. A lid assembly is provided, which includes a lid 66 and plug terminals 68 and 70 having female plug members 68a and 70a, respectively, for receiving conductive pins 40a and 42a, respectively, to connect the associated electrical conductors 44a and 44b to a power supply. With a gel assembly in position, the container 60 is divided into two chambers 62 and 64. With reference to FIG. 4, current flows through the gel assembly from chamber 64 through the top opening in the assembly 50 out the bottom opening of the assembly to chamber 62. If the assembly is inserted into the support plate 10 backwards, current will not flow through the unit. This acts as a safety feature for inexperienced users. The sample DNA in the gel assembly moves from negative to positive or from the top to the bottom of the assembly.

Additionally, referring to FIG. 5, the lid 66 and the positions of the plug terminals 68 and 70 may be configured so that the lid can be placed only in one position so that the proper connections are made to the anode and cathodes. In this regard, the plug assemblies 40 and 42 may be formed off center from the sides of the container on the support members 12 and 14. Accordingly, the plug terminals 68 and 70 are designated cathode or anode and by virtue of their off center position, ensure that the lid fits onto the container in only one configuration.

FIG. 6 illustrates a feature according to the third embodiment of the present invention. In this embodiment, rather than provide mating plug assemblies in the lid of the apparatus, a much more economical structure is provided. All other details of the apparatus being the same, a strip of uninsulated electrically conductive electrode material 69 is provided along each of the vertical support members 12 and 14, one on each side of the support plate, each support member extending above the height of the associated container. A lid 70 includes a receiving block 72 of insulative material for each support member, in which a conductive contact spring 74 is mounted. The contact spring 74 is biased so as to make electrical contact with the conductive strip 69. A lead 76 is connected to the contact spring 74 for connecting with the conductive strip, the cathode or anode of an electrical power supply. A similar arrangement may be achieved with a ball-detent assembly.

The above description is intended by way of example only as is not intended to limit the present invention in any way except as set forth in the following claims.

I claim:

1. In an electrophoresis apparatus including a container for containing conductive buffer solution and means for applying electrical current to said buffer solution, the improvement comprising:

a support plate mounted in said container for receiving a gel assembly, said gel assembly having top and bottom openings therein, said support plate comprising support portions integrally formed therewith for sealing the gel assembly in said container so as to divide said container into laterally juxtaposed first and second chambers when supporting a gel assembly, the top opening being in contact with solution in said first chamber and said bottom opening being in contact with solution in said second chamber, said support portions of said support plate comprising vertical support members having faces cut therein for receiving vertical edges of the gel assembly and an integral bottom support member having a face cut therein for receiving a bottom edge of the gel assembly, the face in said integral bottom support member terminating short of the full width of said vertical support member faces so as to define flanges on which the bottom vertical edges of the gel assembly rest, surface portions of the faces of said vertical support members and said integral bottom support member serving to seal against surface portions of the gel assembly so that the bottom opening of the gel assembly contacts buffer solution in the second chamber through the face of the integral bottom support member; and means for holding said gel assembly upright in said support plate.

2. The improvement of claim 1, wherein said bottom opening of said gel assembly faces downward and said face on said integral bottom support member is flush with the faces on said vertical support members so as to provide access to the bottom opening of said gel assembly and to seal the first chamber from the second chamber when the gel assembly is in place.

3. The improvement of claim 1, wherein said bottom opening of said gel assembly faces laterally towards said support plate and said face on said integral bottom support member is cut deeper than the faces on said vertical support members so as to provide electrical access to the bottom opening of said gel assembly and to seal the first chamber from the second chamber when the gel assembly is in place.

4. The improvement of claim 1, wherein said means for holding comprises resilient clip members attached to said support portions to hold gel assemblies of varying thicknesses.

5. In an electrophoresis apparatus including a container for containing buffer solution and means for applying electrical current to said buffer solution, the improvement comprising:

a support plate mounted in said container for receiving a gel assembly, said gel assembly having top and bottom openings therein, said support plate comprising first and second vertical support members spaced from each other and mounted along opposite vertical walls of said container, and an integral bottom support member mounted on the bottom of said container, each of said first and second vertical support members having a face therein for receiving opposite vertical edges of a gel assembly, said integral bottom support member having a face extending between said first and second vertical support members and terminating short of the full width of said vertical support member faces so as to define flanges at the bottom of said first and second vertical support member faces, said flanges supporting the bottom of said gel assembly, said integral bottom support member sealing against said gel assembly and effectively dividing said container into first and second chambers, said bottom opening of the gel assembly being exposed in said first chamber and the top opening of the gel assembly being exposed in said second chamber; and means for holding said gel assembly upright in said support plate.

6. The apparatus of claim 5, and further comprising:

first and second electrical conductor means disposed in said first and second chambers, respectively;

a lid including first and second leads for connecting with said first and second electrical conductor means, respectively;

first and second male plug members formed integrally with said support plate, and wherein said first electrical conductor strip connects with said first male plug member and is positioned in said first chamber and said second electrical conductor strip connects with said second male plug member and is positioned in said second chamber.

7. The apparatus of claim 6, wherein said lid comprises first and second female plug members to mate with said first and second male plug members, said first and second leads being connected to said first and second female plug members, respectively.

8. An electrophoresis apparatus comprising:

a container for containing buffer solution;

means for applying electrical current to said buffer solution;

a support plate mounted in said container for receiving a gel assembly, said gel assembly having top and bottom openings therein, said support plate comprising support portions integrally formed therewith for sealing the gel assembly in said container so as to divide said container into first and second chambers when supporting a gel assembly, the top opening being in contact with solution in said first chamber and said bottom opening being in contact with solution in said second chamber, said support portions of said support plate comprising vertical support members having faces cut therein for receiving vertical edges of the gel assembly and an integral bottom support member having a face cut therein for receiving a bottom edge of the gel assembly, the face in said integral bottom support member terminating short of the full width of said vertical support member faces so as to define flanges on which the bottom vertical edges of the gel assembly rest, the surfaces of the faces of said vertical support members and said integral bottom support member serving to seal against surface portions of the gel assembly so that the bottom opening of the gel assembly contacts buffer solution in the second chamber through the face of the integral bottom support member;

first and second electrically conductive strips mounted on said support portions and extending into said first and second chambers, respectively; and a lid member for fitting onto said container and including first and second receiving blocks for receiving therein said first and second electrically conductive strips, a contact spring being provided in each receiving block to electrically connect with the corresponding conductive strip, each of said contact springs being electrically connected to an electrical power supply.

* * * * *